(12) United States Patent
Leysieffer (10) Patent No.: US 6,663,575 B2
(45) Date of Patent: Dec. 16, 2003

(54) DEVICE FOR ELECTROMECHANICAL STIMULATION AND TESTING OF HEARING

(75) Inventor: Hans Leysieffer, Taufkirchen (DE)

(73) Assignee: Phonak AG, Stafa (CH)

(*) Notice: Subject to any disclaimer, the term of this patent is extended or adjusted under 35 U.S.C. 154(b) by 0 days.

(21) Appl. No.: 09/938,534

(22) Filed: Aug. 27, 2001

(65) Prior Publication Data

US 2002/0026125 A1 Feb. 28, 2002

(30) Foreign Application Priority Data

Aug. 25, 2000 (DE) .......................... 100 41 725

(51) Int. Cl.⁷ ................................ A61B 5/00
(52) U.S. Cl. ..................... 600/559; 600/25; 600/587
(58) Field of Search ..................... 600/559, 25, 587, 600/595; 607/136, 137

(56) References Cited

U.S. PATENT DOCUMENTS

| | | | |
|---|---|---|---|
| 4,771,792 A | * | 9/1988 | Seale ........................ 600/587 |
| 5,277,694 A | | 1/1994 | Leysieffer et al. |
| 5,776,144 A | | 7/1998 | Leysieffer et al. |
| 5,833,626 A | | 11/1998 | Leysieffer |
| 6,007,494 A | | 12/1999 | Zenner et al. |
| 6,068,590 A | * | 5/2000 | Brisken |

FOREIGN PATENT DOCUMENTS

| | | | |
|---|---|---|---|
| DE | 31 21 429 | 2/1983 | |
| DE | 198 21 602 | 4/2000 | |
| DE | 19821602 C1 | * 4/2000 | ........... A61B/5/103 |

OTHER PUBLICATIONS

Thullen, "Klinische Erfahrungen mit der Schallsonde nch Zollner", pp. 444–445, 1956, Medizinal–Markt, No. 12.

* cited by examiner

Primary Examiner—Max F. Hindenburg
Assistant Examiner—Jonathan Foreman
(74) Attorney, Agent, or Firm—Nixon Peabody LLP; David S. Safran (57) ABSTRACT

A device for electromechanical stimulation and testing of hearing having an electromechanical transducer for producing mechanical stimulation vibrations. The mechanical stimulation vibrations from the electromechanical transducer are non-invasively transmitted through an external auditory canal to at least approximately the center of the tympanic membrane (the umbo) and thus to the manubrium mallei of the ossicular chain. An impedance measuring system measures the mechanical impedance of a biological load structure which is coupled to the transducer.

40 Claims, 5 Drawing Sheets

DEVICE FOR ELECTROMECHANICAL STIMULATION AND TESTING OF HEARING

BACKGROUND OF THE INVENTION

1. Field of the Invention

The invention relates to a device for electromechanical stimulation and testing of hearing, comprising an electromechanical transducer for producing mechanical vibrations, and means for non-invasively transmitting the mechanical stimulation vibrations from the electromechanical transducer through the external auditory canal to at least approximately the center of the tympanic membrane (the umbo) and thus to the manubrium mallei of the ossicular chain.

2. Description of Related Art

Generally the audition of a person is tested in that a sound signal and thus an acoustical wave is presented to the test person in a monaural or binaural manner, and that the test person subjectively reacts on proper questions which are adequate to the respective purpose of the psychoacoustical test. Such electroacoustical devices are generally termed "audiometer", and in most applications the test signal either is generated electronically (by analog or digital signal generators) or is derived from a suitable sound carrier (magnetic tape, compact disc and the like). These test signals then are acoustically presented to the test person, most frequently by loudspeakers under so-called called "free-field" conditions, or by specifically calibrated measuring earphones. In particular cases, for example when an acoustically sealed volume in front of the tympanic membrane is required for the specific test, these acoustical signals are transmitted to the external auditory canal by short sound-conducting hoses and ear pieces.

Furthermore, objective hearing test methods are known (for example BERA: "Brainstem Evoked Response Audiometry") in which acoustically evoked neuronal responses are picked up by skin electrodes and are correspondingly analyzed. Besides, the mobility of the middle ear is routinely determined by a method in which the middle ear is deflected by a pressure buildup within the external auditory canal, whilst one or more test tones are supplied by loudspeakers via transmission hoses, and in which pressure and velocity within the external auditory canal are measured by corresponding transducers (microphones and pressure meters). With the aid of these values, the acoustical impedance and changes thereof caused by pathological changes of the middle ear can be determined. The ability of triggering the stapedius reflex likewise can be measured when properly selecting the configuration of the envelope curve and the level.

In all these methods an acoustical signal is presented which, in a known manner, causes the tympanic membrane to mechanically oscillate, wherein these oscillations are transmitted via the ossicular chain of the middle ear to the inner ear and are converted there into a neuronal stimulation pattern which causes an auditory impression.

Furthermore, laser-audiometrical test devices are known (U.S. Pat. No. 6,007,494) in which dynamic movements of the tympanic membrane and of the manubrium mallei of the ossicular chain, respectively, can be optically, and thus in contactless manner, measured by a laser Doppler vibrometer even in the case of very small motion amplitudes near the auditory threshold in quiet.

In addition there are approaches to carry out examinations of the middle ear by direct contact with an electromechanical transducer (DE-A-31 21 429 and A. Thullen: "Klinische Erfahrungen mit der Schallsonde nach Zöllner", Medizinal-Markt, No. 12, 1956, pp. 444 to 445). In this case a sound probe is contacted with the middle ear, particularly invasively during middle ear operations. A device for pre-operative demonstration for implantable hearing systems and for psychoacoustical measurement of the auditory threshold in quiet by direct mechanical stimulation of the umbo is known from U.S. Pat. No. 5,833,626. This device comprises an electromechanical transducer for generating mechanical vibrations in the audio range, and a rigid mechanical coupling member for transmitting the mechanical vibrations, without surgery, through the external auditory canal in direct mechanical contact to the center of the tympanic membrane and thus to the manubrium mallei of the ossicular chain of the middle ear. Systems for non-invasively coupling such a device to the extra-corporal side of the tympanic membrane are described in U.S. Pat. No. 5,776,144.

German Patent No. 19 821 602 discloses a vibration measuring head comprising an electromechanical transducer, which head permits, exclusively in resonance operation, an evaluation of the movability of the vibratorily movable elements of the middle ear structure coupled to the actoric side of the transducer by means of a second measuring coil because the dampening of the system by the middle ear structure coupled thereto is represented by a variation of the voltage generated by this coil.

Especially in the described objective hearing testing methods (for example, BERA) there are, however, some disadvantages in the type of acoustic excitation, such as for example the magnetic fields generated by the usually used electrodynamic or electromagnetic headphones. These magnetic (interference) fields lead to problems in pre-processing and analysis of the evoked potentials which are electrically derived from the skin surface of the head and which can be in the nV range. For acoustic signals monaurally presented supraliminally at medium to high sound levels the problem of "overhearing" of the contralateral ear, which is not being tested, due to the acoustic sound emission of the headphone or by body sound (bone conduction) continues to occur, which leads to the necessity of acoustic masking of the contralateral ear. This effect is undesirable in many psychoacoustic situations, but inevitable. A disadvantage in using the device known from German Patent No. 198 21 602 particularly is that a broad-band measurement is impossible because the method applied is based on resonance effects of the transducer. Thus a true determination of the mechanical impedance of the middle ear structure coupled to the device is not possible, particularly when measurements in different spectral regions are desired. However, measurements in different spectral regions, at least within the main speech frequency range, are of substantial importance when precise information about the pathological condition of the middle ear or even of the inner ear, which is mechanically coupled thereto, is to be obtained.

SUMMARY OF THE INVENTION

A primary object of the present invention is to provide for a device for electromechanical stimulation and testing of hearing which permits in a particularly reliable manner a non-invasive objective testing of a person's auditory capacity.

According to the invention, this object basically is achieved by a device for electromechanical stimulation and testing of hearing, comprising an electromechanical transducer for producing mechanical stimulation vibrations; means for non-invasively transmitting the mechanical stimulation vibrations from the electromechanical transducer through the external auditory canal to at least approximately the center of the tympanic membrane (the umbo) and thus to the manubrium mallei of the ossicular chain; and an impedance measuring system for measuring the mechanical impedance of a biological load structure which is coupled to the transducer.

The presently used electromechanical transducer basically may be designed in conformity with any known transducer principle. Thus, this transducer particularly may be an electromagnetic, electrodynamic, magnetostrictive, dielectric and particularly piezoelectric transducer.

In conformity with one embodiment of the invention, the impedance measuring system may comprise means for measuring the electrical input impedance of the electromechanical transducer which is coupled to the biological load structure. The data for magnitude and phase of this electrical input impedance reflect the load components coupled to the device because these load components, transformed via the electromechanical coupling of the transducer, appear on the electrical side and thus can be measured.

Preferably, the electromechanical transducer is driven by a driver unit to which the transducer is connected via a measuring resistance across which a measuring voltage proportional to a transducer current is dropped, and a measuring amplifier is provided which has applied thereto, as input signals, said measuring voltage and a transducer terminal voltage. In order to preclude a corruption of the measurements, the voltage drop across the measuring resistance preferably is taken off in a floating and high impedance manner, and the measuring resistance advantageously is dimensioned such that the sum of the resistance value of the measuring resistance and of the absolute value of the complex electrical input impedance of the electromechanical transducer coupled to the biological load structure is large with respect to the internal resistance of the driver unit. Furthermore, preferably digital, means are provided for forming the quotient of the transducer terminal voltage and the transducer current.

According to an alternate embodiment of the invention the impedance measuring means, however, also may be designed for direct measurement of the mechanical impedance of the biological load structure coupled to the electromechanical transducer, and such impedance measuring means may be integrated into the transducer at the actoric output side thereof. Preferably, the impedance measuring means is designed for generating measuring signals which are at least approximately proportional as to magnitude and phase to the force acting on the biological load structure and the velocity of the transmitting means, respectively. In such a case, the system advantageously further includes a two-channel measuring amplifier and, preferably digital, means for providing the quotient of the measuring signal corresponding to the force acting on the biological load structure and of the measuring signal corresponding to the velocity of the of the transmitting means.

In the case of the direct impedance measurement the electromechanical transducer and the impedance measuring means may be disposed within a common housing which optionally also receives the measuring amplifier.

The described impedance measurements by no means are restricted to a single measuring frequency or to a single measuring level. Rather, advantageously for indirect as well as for direct measurement of the mechanical impedance of the biological load structure, preferably digital, means are provided for measuring the mechanical impedance of the biological load structure coupled to the electromechanical transducer as a function of the frequency and/or of the level of the stimulation signal delivered by the transducer. Measurements extending over the entire transmission frequency range and the entire stimulation level range are particularly suited to gain important detailed information about linear and particularly non-linear variations of the middle ear and/or the inner ear. Thus, for example, it may be expected that a mechanical non-linearity of the middle ear caused for example by a partial luxation of a middle ear ossicle, can be detected by varying the electrical level during the impedance measurement.

When a level analysis as to non-linearities over the entire useful level range is dispensed with, and when the measuring system is of a sufficiently sensitive and low-noise type, the measurement of the electrical transducer impedance also may be carried out below the individual patient's auditory threshold in quiet in order to avoid any disturbance of the patient by the measuring signals.

In conformity with a further embodiment of the invention, preferably digital, means may be provided for detecting the spectral distribution of resonance frequencies in the course of the impedance measured as a function of the frequency of the stimulation signal, and also means for detecting the difference between the measured impedance values occurring at the resonance frequencies. This difference gives information as to the mechanical oscillation Q-values.

Preferably, a passive coupling element is provided for coupling the electromechanical transducer to the umbo. The impedance measuring system for direct measurement of the mechanical impedance may be incorporated into this coupling element.

In conformity with an embodiment of the invention the electromechanical transducer may be disposed within a housing the geometrical dimensions of which are selected such that, upon placing the transducer in an entrance region of the external auditory canal, the person carrying out the test, even when using a microscope, has an unobstructed view onto the actor end of the coupling element mechanically contacting the umbo.

The coupling rod preferably is designed in a manner which allows to easily manually curve or bend the coupling rod, whereby the coupling rod can be simply adapted to individual geometrical shapes of the external auditory canal. Furthermore, the coupling element advantageously is not mechanically fixedly, but rather detachably connected to the electromechanical transducer, preferably by means of plug-type connector means. This, for example, permits the utilization of various different coupling elements which, for hygienical reasons, can be designed as easily exchangeable single-use articles.

Preferably, the first mechanical resonance frequency of a combination comprised of the electromechanical transducer and the mechanical coupling element is disposed at the upper end of the spectral transmission range of at least 10.000 cps. Such a broad-band design provides for short transient periods.

According to a further embodiment of the invention the electromechanical transducer has a mechanical source impedance which, in the entire spectral transmission range, is distinctly higher than the mechanical load impedance defined by a biological system comprising the tympanic membrane, the ossicular chain and the inner ear. This provides for an impression of the deflection of the actor end of the coupling element which is independent of individual variations of the biological load impedance.

Preferably the electromechanical transducer and a driver unit driving the latter are designed such that the transducer and the mechanical coupling element, with the ossicular chain being coupled thereto, in the entire spectral transmission range, have maximum amplitudes of deflection in the region from 1 to 5 micrometers corresponding to equivalent sound pressure levels from 120 to 140 dB SPL.

Advantageously the electromechanical transducer is encapsulated for minimizing the sound signal emitted by the oscillating transducer structures. Thereby an acoustic masking of the contralateral ear which is not tested frequently can be dispensed with even at high stimulation levels.

The device may be provided in duplicate for simultaneously stimulating and testing both ears of a test person.

These and further objects, features and advantages of the present invention will become apparent from the following description when taken in connection with the accompanying drawings which, for purposes of illustration only, shows several embodiments in accordance with the present invention.

DETAILED DESCRIPTION OF THE INVENTION

Figure 1:
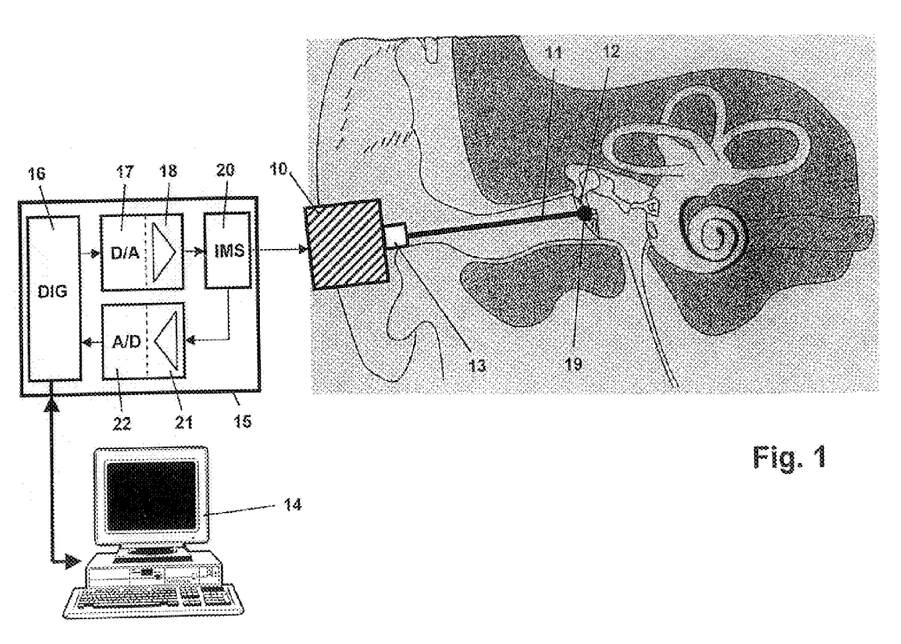
FIG. 1 shows an embodiment of an arrangement for objevtively testing the hearing.

The arrangement of FIG. 1 comprises an electromechanical transducer 10 for producing mechanical vibrations, and a coupling element 11 for transmitting these vibrations to at least approximately the center of the tympanic membrane (the umbo) and thus to the manubrium mallei of the ossicular chain. In the illustrated embodiment coupling element 11 is a coupling rod. The coupling rod may be connected to the actoric output side of transducer 10 in a fixed manner or in a detachable manner using for example plug-type connector means as schematically indicated at 13. The actoric end 19 of coupling rod 11, which is remote from transducer 10, is designed in a manner providing for a non-traumatic mechanical contact with the umbo. Systems as known from the above mentioned U.S. Pat. No. 5,776,144 may be used for positioning the transducer 10 and the coupling element 11.

The electrical signals for driving the transducer preferably are produced in digital form by a computer 14 and are transmitted to a hardware interface 15, for example via a serial standard interface such as RS 232. The interface 15 comprises a digital interface (DIG) 16, which transmits the digitally generated signal of computer 14 to a digital to analog converter 17 and a subsequent driver 18. Driver 18 is adapted to the respective transducer principle of the electromechanical transducer 10. An impedance measuring system (IMS) 20 for an analog measurement of the electrical input impedance of the electromechanical transducer 10 is connected between driver 18 and the electromechanical transducer 10. The analog measuring data supplied by the impedance measuring system 20 are converted into digital measuring data by a measuring amplifier 21 and an associated analog to digital converter (A/D) 22. The digital measuring data are supplied via digital interface 16 to computer 14 for further processing, evaluation, display and storing.

Figure 2:
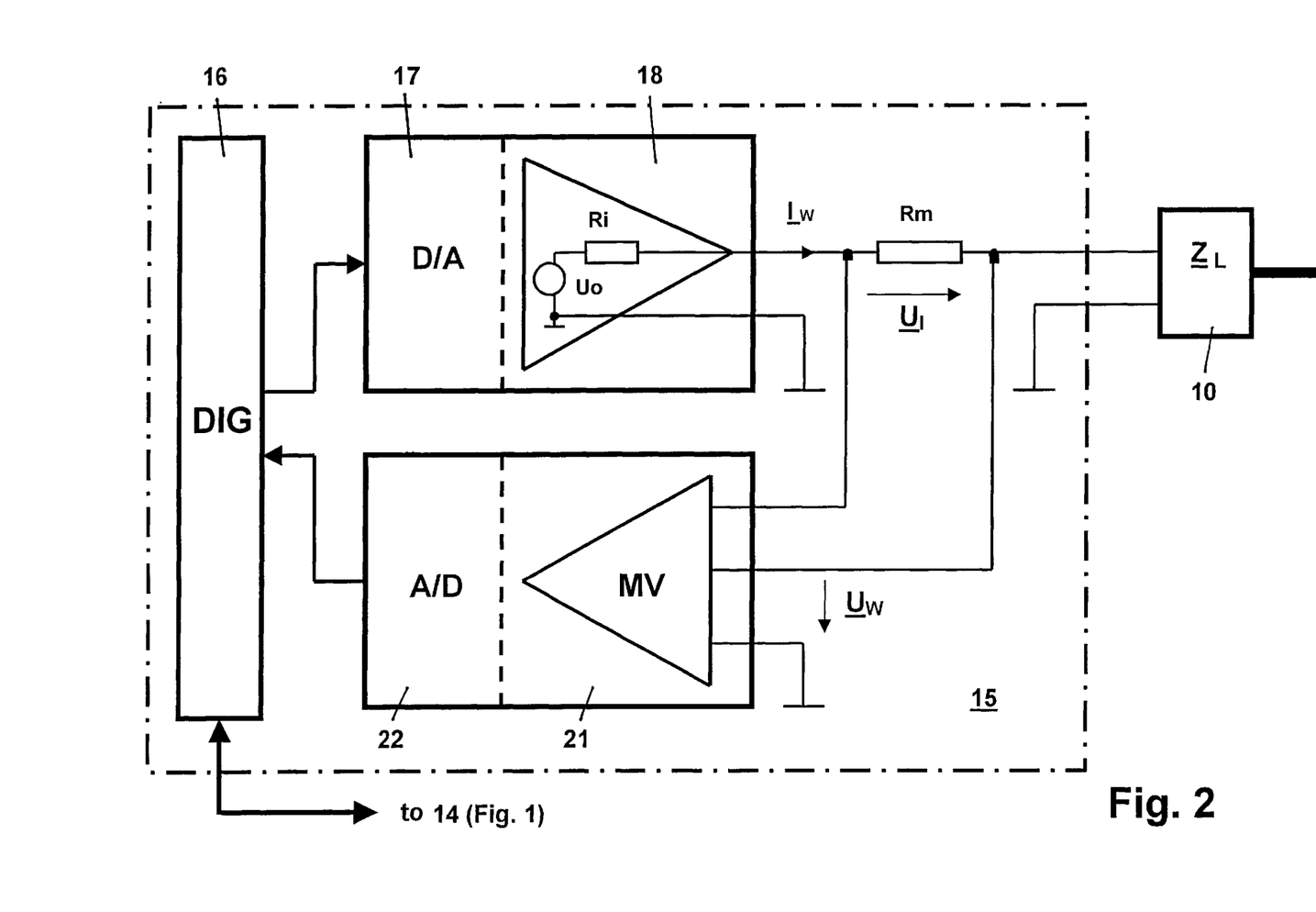
FIG. 2 shows an embodiment of an impedance measuring system for the arrangement according to FIG. 1.

FIG. 2 shows a simple embodiment of the impedance measurement system 20 according to FIG. 1. The digital driver data for the electromechanical transducer 10, which data are coming from the digital interface 16, are converted by the digital analog converter 17 into an analog signal and are routed to the transducer driver 18, In the subject embodiment, the output of driver 18 is illustrated as a voltage source $U_o$ having an internal resistance $R_i$. The analog output signal of driver 18 is sent, via a measuring resistance $R_m$, to the electromechanical transducer 10 which has a complex electrical impedance $\underline{Z}_L$.

When the sum of $R_m$ and of the absolute value of $\underline{Z}_L$ is large with respect to $R_i$, voltage is impressed on the electromechanical transducer 10. When the voltage drop across $R_m$ is picked up by the illustrated measuring amplifier (MV) 21 in a floating and high impedance manner, a measuring voltage $\underline{U}_I$ is available which is proportional to the transducer current $\underline{I}_W$. At the same time, the transducer terminal voltage $\underline{U}_W$ is available to the measuring amplifier 21. After a corresponding analog to digital conversion of these measuring voltages in analog to digital converter 22, both data sets are available in digital form to the digital interface 16. Thus it is possible to determine the complex electrical transducer impedance $\underline{Z}_L = \underline{U}_W/\underline{I}_W$ as to magnitude and phase by a digital formation of the corresponding quotient.

Figures 3, 4, 5:
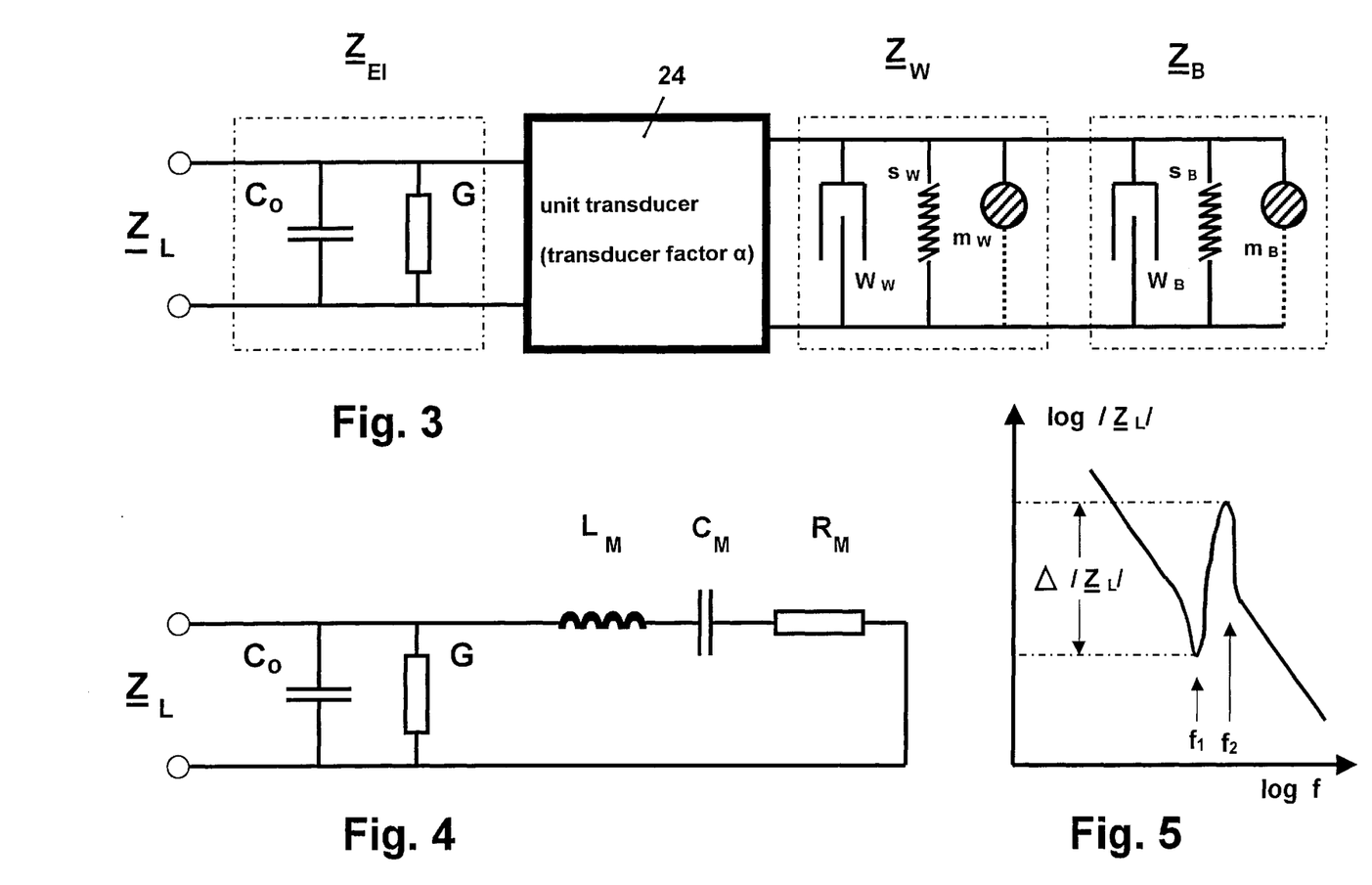
FIG. 3 shows an electromechanical equivalent circuit diagram approximating a piezoelectric transducer and biological load components coupled thereto.
FIG. 4 shows an equivalent circuit diagram of the electrical transducer impedance $\underline{Z}_L$ according to FIG. 3.
FIG. 5 shows the dependency of the absolute value of the electrical transducer impedance $/\underline{Z}_L/$ on the frequency $f$ according to FIG. 4 in double-logarithmic representation.

FIG. 3 shows an electromechanical equivalent circuit diagram approximating a piezoelectric transducer and biological load components coupled thereto. The piezoelectric transducer is determined, at the electrical impedance side $\underline{Z}_{El}$, essentially by a quiescent capacity $C_o$ and a leakage conductance G. An electromechanical unit transducer 24 having an electromechanical transducer factor α is followed by the mechanical components of the transducer itself, which represent the mechanical transducer impedance $\underline{Z}_W$. When a piezoelectric transducer is operated in a high-frequency mode, i.e. when the first mechanical resonance frequency is disposed at the upper end of the spectral transmission range, as discussed in more detail in U.S. Pat. No. 5,277,694, the mechanical transducer impedance $\underline{Z}_W$ is properly determined in conformance with a first approximation by the mechanical components: dynamic transducer mass $m_W$, transducer stiffness $s_W$ and the frictional transducer resistance (real proportion) $W_W$. The biological mechanical load impedance $\underline{Z}_B$ in the subject example likewise is approximated by the three mechanical impedance components: mass $m_B$ (for example the mass of the middle ear ossicles), stiffness $s_B$ (for example the stiffness of the ligaments supporting the middle ear ossicles and of the annular ligament holding the stapes footplate in the oval window) and frictional resistance $W_B$. Under the assumption that at the side of the mechanical load the transducer components as well as the biological load components have the same velocity (mechanical parallel connection), an electrical equivalent circuit diagram as shown in FIG. 4 is obtained upon transformation of the mechanical components by the unit transducer 24 onto the electrical side.

FIG. 4 shows the equivalent circuit diagram of the electrical transducer impedance $\underline{Z}_L$ according to FIG. 3, wherein the inductivity $L_M$ reflects the sum of the masses $m_W$ and $m_B$, the capacity $C_M$ represents the mechanical parallel connection of the stiffnesses $s_W$ and $S_B$, and the resistance $R_M$ corresponds to the mechanical parallel connection of the components $W_W$ and $W_B$.

FIG. 5 shows the dependency of the absolute value of the electrical transducer impedance $/\underline{Z}_L/$ on the frequency $f$ according to FIG. 4 in double-logarithmic representation. The basically capacitive course of $/\underline{Z}_L/$ determined by $C_o$ is to be recognized. The series resonance occurring at $f_1$ and the parallel resonance occurring at $f_2$ are determined by the components $L_M$ and $C_M$ together with $C_o$. The value $\Delta/\underline{Z}_L/$ gives information about the mechanical oscillation Q. Therefore very accurate information about the biological load components can be gained from the spectral positions of $f_1$ and $f_2$ and from the value $\Delta/\underline{Z}_L/$, particularly when the impedance measurements represent the entire spectral range and the entire level range of the hearing range (for example 20 cps to 15.000 cps and an equivalent stimulation level from the auditory threshold in quiet (about 0 to 40 dB SPL) up to the discomfort limit corresponding to about 100 to 120 dB SPL). Resonances of higher order are not illustrated in FIG. 5. Such higher order resonances can be assumed to occur in the course of real measurements, but they basically follow the same transformation laws as presently described, and therefore they can be measured in an equally precise manner, so that additional information about the measured load structure can be obtained.

Figure 6:
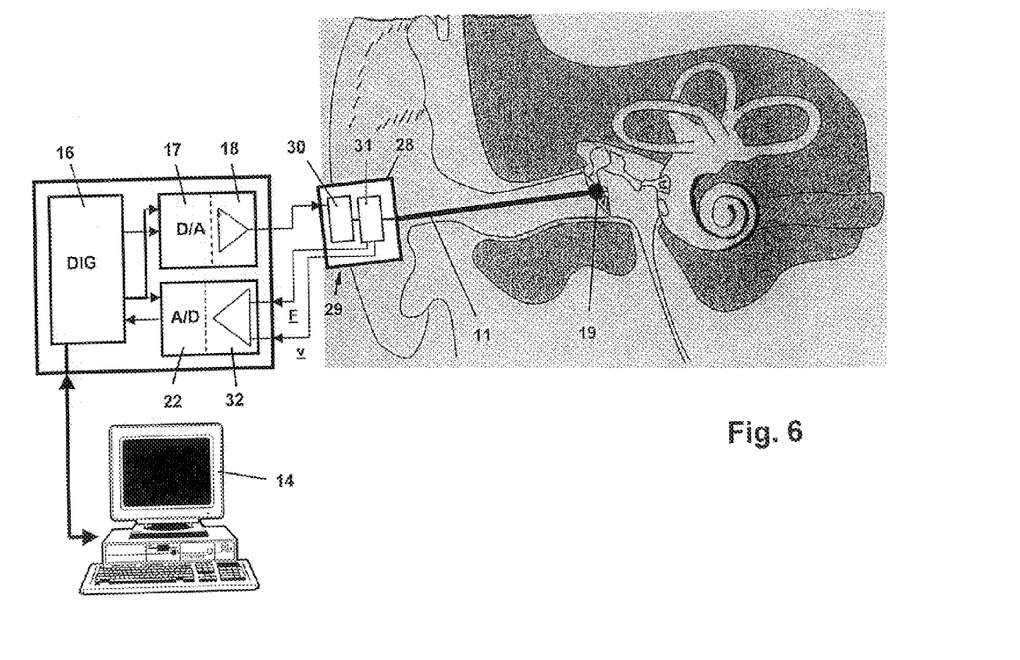
FIG. 6 shows an embodiment of an arrangement with direct mechanical impedance measurement.

FIG. 6 shows a system for a non-invasive measurement of the mechanical impedance of the hearing which is substantially similar to the system of FIG. 1, however is modified to provide for a direct measurement of the mechanical impedance. Connected to the digital to analog converter 17 and to the driver amplifier 18, which is adapted to the transducer principle used, is a unit 29 which is received in a housing 28 and which includes an electromechanical transducer 30 having an electromechanically active element, for example a piezoelectric and/or electromagnetic system. A mechanical impedance measuring system 31 is integrated into the transducer housing at the actoric output side of the transducer. The impedance measuring system 31 measures the magnitude and phase of the force $\underline{F}$ acting on the biological load structure and of the velocity $\underline{v}$ of a coupling element 11 that is contacted with the umbo.

The impedance measuring system 31 supplies electrical, analog measuring signals which are proportional to the force $\underline{F}$ and to the velocity $\underline{v}$, respectively. These analog measuring signals are converted into digital measuring data by a two-channel measuring amplifier 32 and the associated analog to digital converter 22, and they are routed to the digital interface 16. The formation of the complex mechanical impedance $\underline{Z}(f, P) = \underline{F}/\underline{v}$ as a function of the frequency $f$ and of the measuring level P can be accomplished either in the computer 14 or already in the digital interface 16 provided that respective computer structures are present within the latter. The crude impedance data are made available to computer 14 for further processing, evaluation, display and storing.

Figure 7:
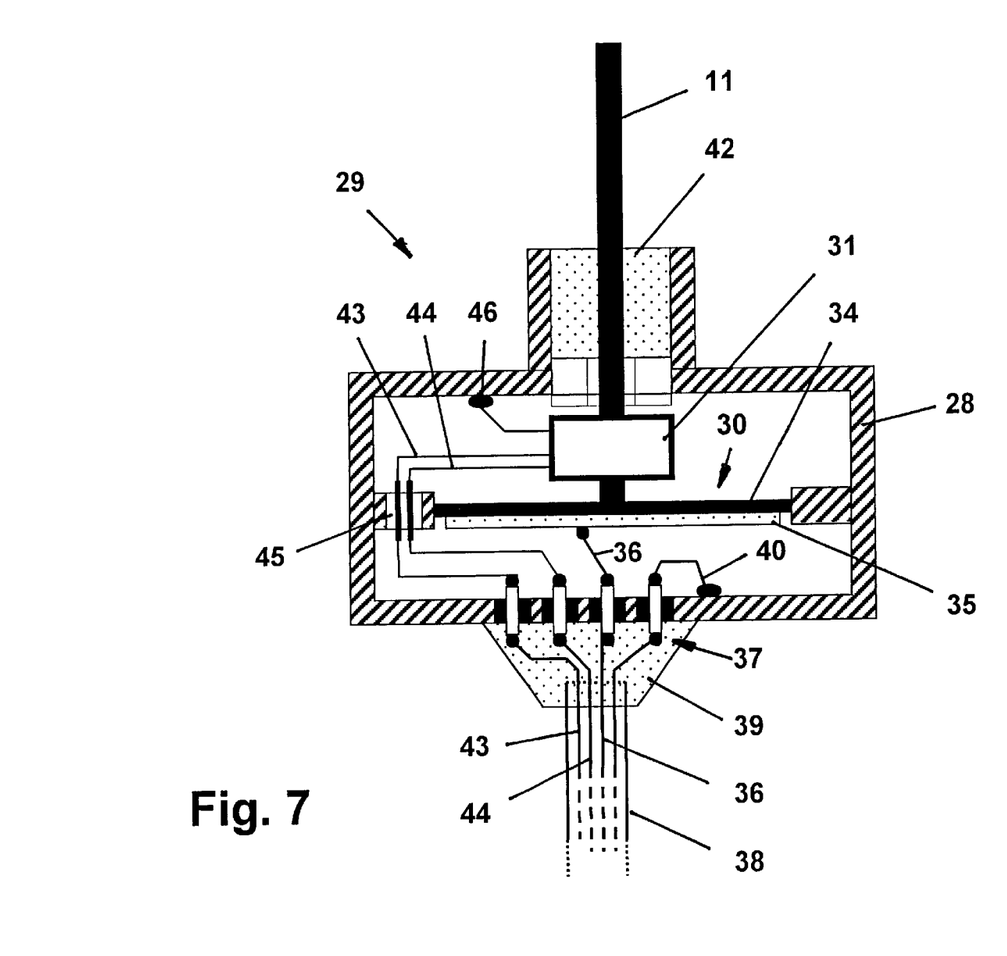
FIG. 7 shows an embodiment of a piezoelectrical transducer system provided with a measuring system for direct mechanical impedance measurement in conformity with FIG. 6.

FIG. 7 shows an embodiment of the unit 29 of FIG. 6 comprising a piezoelectric transducer system in conformity with U.S. Pat. No. 5,277,694 and additionally a measuring system for directly determining the mechanical impedance. The unit 29 illustrated in FIG. 7 is provided with a biocompatible cylindrical housing 28 of electrically conductive material, such as titanium. The housing 28 is filled with an inert gas. An electrically conductive membrane 34 of electromechanical output transducer 30 that can oscillate, is disposed within the housing 28. The membrane 34 preferably is circular, and it is fixedly connected to housing 28 at the outer edge thereof. A thin disk 35 of piezoelectric material, e.g. lead-zirconate-titanate (PTZ), is provided at the side of membrane 34, which in FIG. 7 is the underside. The side of the piezoelectric disk 35 facing membrane 34 is in electrically conductive connection with membrane 34, preferably via an electrically conductive adhesive connection. The piezoelectric disk 35 is contacted, at the side thereof remote from membrane 34, with a thin flexible wire which is part of a signal line 36 and which in turn is connected, via a hermetically sealed housing feed-through connector 37, to a transducer line 38 which is disposed outside of housing 28. A polymer sealing between the outer side of housing 28, the housing feed-through connector 37 and the transducer line 38 is shown in FIG. 7 at 39. A ground terminal 40 extends from transducer line 38 via the housing feed-through connector 37 to the inner side of housing 28.

Application of an electrical voltage between the signal line 36 and the ground terminal 40 results in a deformation of the hetero-compound consisting of membrane 34 and piezoelectric disk 35, and thus in a deflection of membrane 34. Further particulars of such a piezoelectric transducer which may be utilized in the present system, too, are described in commonly owned U.S. Pat. No. 5,277,694 which is hereby incorporated by reference. Such an electromechanical output transducer 30 typically has a relatively high mechanical output impedance, particularly a mechanical output impedance which is higher than the mechanical load impedance of the biological structure of the middle ear and/or the inner ear coupled to the transducer during the measurement.

Coupling of the output side of transducer 30 to the biological load structure takes place via the coupling rod 11 and the mechanical impedance measuring system 31 which is in mechanical connection with the side of membrane 34 which in FIG. 7 is the upper side of membrane 34; preferably the connection is with the center of the membrane. The impedance measuring system 31, with its end facing the membrane 34, may directly engage membrane 34, and with its other end, may engage the end of coupling rod 11 facing the membrane; however, impedance measuring system 31 also may be integrated into coupling rod 11.

In the illustrated embodiment coupling rod 11 extends at least approximately normal to membrane 34 from the outside into the interior of housing 28 through an elastically resilient polymer sealing 42. The polymer sealing 42 is designed such as to permit axial oscillations of the coupling rod 11.

The impedance measuring system 31 is disposed within housing 28. The analog measuring signals corresponding to the force $\underline{F}$ and to the velocity $\underline{v}$ are transmitted from the impedance measuring system 31 via measuring lines 43, 44, feed-through connectors 45 within the housing and the housing feed-through connector 37 to the transducer line 38. The impedance measuring system 31 further is in electrically conductive connection via a ground terminal with housing 28 and via this housing with the ground terminal 40. Thus the reference potential of the two measuring signals for force and velocity is the transducer housing 28. When, in conformity with a preferred embodiment, the impedance measuring system 31 itself is based on piezoelectric transducers and therefore active electrical impedance converters are required in the measuring system, the latter may be supplied via electric phantom feed means with operating energy from the hardware interface 15 through one of the two measuring lines 43, 44 for force or velocity.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

I claim:

1. A device for electromechanical stimulation and testing of hearing, comprising:
   an electromechanical transducer for producing mechanical stimulation vibrations;
   means for non-invasively transmitting the mechanical stimulation vibrations from the electromechanical transducer through the external auditory canal to approximately the center of the tympanic membrane (the umbo) and thus to the manubrium mallei of the ossicular chain; and
   an impedance measuring system for measuring the mechanical impedance of a biological load structure which is coupled to the transducer by forming a quotient of a first measuring signal and a second measuring signal,
   wherein the impedance measuring system comprises means for measuring the electrical input impedance of the electromechanical transducer coupled to the biological load structure.

2. The device as claimed in claim 1, wherein the electromechanical transducer is driven by a driver unit having an internal resistance, to which driver unit the transducer is connected via a measuring resistance across which a measuring voltage proportional to a transducer current is dropped, and wherein a measuring amplifier is provided, which measuring amplifier has applied thereto as said first and second measuring signals said measuring voltage and a transducer terminal voltage.

3. The device as claimed in claim 2, comprising means for obtaining the measuring voltage drop in a floating and high-impedance manner.

4. The device as claimed in claim 2, wherein the measuring resistance is dimensioned such that the sum of the resistance value of the measuring resistance and of the absolute value of the complex electrical input impedance of the electromechanical transducer coupled to the biological load structure is large with respect to the internal resistance of the driver unit.

5. The device as claimed in claim 2, comprising means for providing the quotient of the transducer terminal voltage and of the transducer current.

6. The device as claimed in claim 1, comprising means for measuring the mechanical impedance of the biological load structure coupled, during testing of the hearing, to the transducer as a function of at least one selected from the group consisting of the frequency and the level of a stimulation signal delivered by the transducer.

7. The device as claimed in claim 6, comprising means for detecting a spectral distribution of resonance frequencies in the course of the mechanical impedance measured as a function of the frequency of the stimulation signal.

8. The device as claimed in claim 1, comprising a passive mechanical coupling element for coupling the electromechanical transducer to the umbo.

9. The device as claimed in claim 8, wherein the coupling element, comprises a coupling rod which, in axial direction thereof, is stiff with respect to the vibrations to be transmitted thereby, and the end of which that is remote from the transducer is designed for a non-traumatic mechanical contact with the umbo.

10. The device as claimed in claim 9, wherein the coupling rod is adapted to be easily manually curved.

11. The device as claimed in claim 8, wherein the electromechanical transducer is disposed within a housing the geometrical dimensions of which are selected such that, upon placing the transducer in an entrance region of the external auditory canal, an unobstructed view onto the end of the coupling element mechanically contacting the umbo is preserved.

12. The device as claimed in claim 8, wherein the coupling element is detachably connected to the electromechanical transducer.

13. The device as claimed in claim 8, wherein a first mechanical resonance frequency of a combination comprised of the electromechanical transducer and the mechanical coupling element is disposed at the upper end of a spectral transmission range of at least 10.000 cps.

14. The device as claimed in claim 8, wherein the electromechanical transducer and a driver unit driving the latter are designed for the transducer and the mechanical coupling element with the ossicular chain being coupled thereto in the entire spectral transmission range, having maximum amplitudes of deflection from 1 to 5 micrometers corresponding to equivalent sound pressure levels from 120 to 140 dB SPL.

15. The device as claimed in claim 1, comprising means for simultaneously stimulating and testing both ears of a test person.

16. A device for electromechanical stimulation and testing of hearing, comprising:
   an electromechanical transducer for producing mechanical stimulation vibrations;
   means for non-invasively transmitting the mechanical stimulation vibrations from the electromechanical transducer through the external auditory canal to approximately the center of the tympanic membrane (the umbo) and thus to the manubrium mallei of the ossicular chain; and
   an impedance measuring system for measuring the mechanical impedance of a biological load structure which is coupled to the transducer by forming a quotient of a first measuring signal and a second measuring signal,
   wherein the impedance measuring system is designed for direct measurement of the mechanical impedance of the biological load structure coupled, during testing of the hearing, to the transducer and is integrated into the transducer at an actoric output side thereof.

17. The device as claimed in claim 16, wherein the impedance measuring system is designed for generating, as said first and second measuring signals, measuring signals which are approximately proportional as to absolute value and phase to one selected from the group consisting of forces acting on the biological load structure and the velocity of the transmitting means.

18. The device as claimed in claim 17, comprising means for providing the quotient of the measuring signal corresponding to the force acting on the biological load structure and of the measuring signal corresponding to the velocity of the transmitting means.

19. The device as claimed in claim 16, comprising means for measuring the mechanical impedance of the biological load structure coupled, during testing of the hearing, to the transducer as a function of at least one selected from the group consisting of the frequency and the level of a stimulation signal delivered by the transducer.

20. The device as claim in claim 19 comprising means for detecting a spectral distribution of resonance frequencies in the course of the mechanical impedance measured as a function of the frequency of the stimulation signal.

21. The device as claimed in claim 16, comprising a passive mechanical coupling element for coupling the electromechanical transducer to the umbo.

22. The device as claimed in claim 21, wherein the coupling element, comprises a coupling rod which, in axial direction thereof, is stiff with respect to the vibrations to be transmitted thereby, and the end of which that is remote from the transducer is designed for a non-traumatic mechanical contact with the umbo.

23. The device as claimed in claim 22, wherein the coupling rod is adapted to be easily manually curved.

24. The device as claimed in claim 21, wherein the electromechanical transducer is disposed within a housing the geometrical dimensions of which are selected such that, upon placing the transducer in an entrance region of the external auditory canal, an unobstructed view onto the end of the coupling element mechanically contacting the umbo is preserved.

25. The device as claimed in claim 21, wherein the coupling element is detachably connected to the electromechanical transducer.

26. The device as claimed in claim 21, wherein a first mechanical resonance frequency of a combination comprised of the electromechanical transducer and the mechanical coupling element is disposed at the upper end of a spectral transmission range of at least 10.000 cps.

27. The device as claimed in claim 21, wherein the electromechanical transducer and a driver unit driving the latter are designed for the transducer and the mechanical coupling element with the ossicular chain being coupled thereto in the entire spectral transmission range, having maximum amplitudes of deflection from 1 to 5 micrometers corresponding to equivalent sound pressure levels from 120 to 140 dB SPL.

28. The device as claimed in claim 16, comprising means for simultaneously stimulating and testing both ears of a test person.

29. A device for electromechanical stimulation and testing of hearing, comprising:
   an electromechanical transducer for producing mechanical stimulation vibrations;
   means for non-invasively transmitting the mechanical stimulation vibrations from the electromechanical transducer through the external auditory canal to approximately the center of the tympanic membrane (the umbo) and thus to the manubrium mallei of the ossicular chain;
   an impedance measuring system for measuring the mechanical impedance of a biological load structure which is coupled to the transducer by forming a quotient of a first measuring signal and a second measuring signal; and
   a passive mechanical coupling element for coupling the electromechanical transducer to the umbo,
   wherein the impedance measuring system is integrated into the coupling element.

30. The device as claimed in claim 29, wherein the coupling element, comprises a coupling rod which, in axial direction thereof, is stiff with respect to the vibrations to be transmitted thereby, and the end of which that is remote from the transducer is designed for a non-traumatic mechanical contact with the umbo.

31. The device as claimed in claim 30, wherein the coupling rod is adapted to be easily manually curved.

32. The device as claimed in claim 29, wherein the electromechanical transducer is disposed within a housing the geometrical dimensions of which are selected such that, upon placing the transducer in an entrance region of the external auditory canal, an unobstructed view onto the end of the coupling element mechanically contacting the umbo is preserved.

33. The device as claimed in claim 29, wherein the coupling element is detachably connected to the electromechanical transducer.

34. The device as claimed in claim 29, wherein a first mechanical resonance frequency of a combination comprised of the electromechanical transducer and the mechanical coupling element is disposed at the upper end of a spectral transmission range of at least 10.000 cps.

35. The device as claimed in claim 34, wherein the electromechanical transducer has a mechanical source impedance which, in the entire spectral transmission range is distinctly higher than a mechanical load impedance defined by a biological system comprising tympanic membrane, ossicular chain and inner ear.

36. The device as claimed in claim 29, wherein the electromechanical transducer and a driver unit driving the latter are designed for the transducer and the mechanical coupling element with the ossicular chain being coupled thereto in the entire spectral transmission range, having maximum amplitudes of deflection from 1 to 5 micrometers corresponding to equivalent sound pressure levels from 120 to 140 dB SPL.

37. The device as claimed in claim 29, comprising means for simultaneously stimulating and testing both ears of a test person.

38. A device for electromechanical stimulation and testing of hearing, comprising:

an electromechanical transducer for producing mechanical stimulation vibrations;

means for non-invasively transmitting the mechanical stimulation vibrations from the electromechanical transducer through the external auditory canal to approximately the center of the tympanic membrane (the umbo) and thus to the manubrium mallei of the ossicular chain;

a passive mechanical coupling element for coupling the electromechanical transducer to the umbo; and an impedance measuring system for measuring the mechanical impedance of a biological load structure which is coupled to the transducer by forming a quotient of a first measuring signal and a second measuring signal, wherein a first mechanical resonance frequency of a combination composed of the electromechanical transducer and the mechanical coupling element is disposed at the upper end of a spectral transmission range of at least 10.000 cps and wherein the electromechanical transducer has a mechanical source impedance which, in the entire spectral transmission range is distinctly higher than a mechanical load impedance defined by a biological, system comprising tympanic membrane, ossicular chain and inner ear.

39. The device as claimed in claim 38, wherein the electromechanical transducer and a driver unit driving the latter are designed for the transducer and the mechanical coupling element with the ossicular chain being coupled thereto in the entire spectral transmission range, having maximum amplitudes of deflection from 1 to 5 micrometers corresponding to equivalent sound pressure level from 120 to 140 dB SPL.

40. The device as claimed in claim 38, comprising means for simultaneously stimulating and testing both ears of a test person.

\* \* \* \* \*